United States Patent

Baylink et al.

[11] Patent Number: 5,691,305
[45] Date of Patent: Nov. 25, 1997

[54] BONE IMPLANT COMPOSITION COMPRISING A POROUS MATRIX, BONE GROWTH PROMOTER PROTEINS, AND PHOSPHOTYROSYL PROTEIN PHOSPHATASE INHIBITOR

[76] Inventors: David J. Baylink, 1428 Serpentine Dr., Redlands, Calif. 92373; Rolf Ewers, 1160 Wien, Liebhardtstalstr. 28, Austria; Axel Kirsch, 7024 Filderstadt, Talstrasse 23, Germany

[21] Appl. No.: 515,700

[22] Filed: Aug. 16, 1995

Related U.S. Application Data

[63] Continuation of Ser. No. 387,137, Feb. 10, 1995, abandoned, which is a continuation of Ser. No. 50,405, filed as PCT/DE92/00780, Sep. 9, 1992, abandoned.

[30] Foreign Application Priority Data

Sep. 13, 1991 [DE] Germany .................. 41 30 546.9

[51] Int. Cl.⁶ .................. A61K 38/18; A61K 38/22; A61K 33/24
[52] U.S. Cl. .................. 514/8; 530/350; 530/399; 435/69.1; 514/12; 604/891.1
[58] Field of Search .................. 530/350, 399; 435/69.1; 514/8, 12; 623/16; 604/891.1

[56] References Cited

U.S. PATENT DOCUMENTS

| | | | |
|---|---|---|---|
| 4,911,931 | 3/1990 | Baylink | 424/606 |
| 4,968,590 | 11/1990 | Kuberasampath et al. | 530/326 |
| 5,013,728 | 5/1991 | Grodberg | 514/171 |
| 5,118,667 | 6/1992 | Adams et al. | 514/12 |
| 5,141,905 | 8/1992 | Rosen et al. | 435/69.1 |
| 5,158,934 | 10/1992 | Ammann et al. | 514/12 |
| 5,166,058 | 11/1992 | Wang et al. | 435/69.1 |
| 5,208,219 | 5/1993 | Ogawa et al. | 514/12 |
| 5,236,456 | 8/1993 | O'Leary et al. | 623/16 |
| 5,263,985 | 11/1993 | Bao et al. | 623/16 |
| 5,264,214 | 11/1993 | Rhee et al. | 424/422 |
| 5,270,300 | 12/1993 | Hunziker | 514/12 |
| 5,290,494 | 3/1994 | Coombes et al. | 264/41 |

FOREIGN PATENT DOCUMENTS

| | | |
|---|---|---|
| 0 322 249 | 6/1989 | European Pat. Off. |
| WO90/04974 | 5/1990 | WIPO |

OTHER PUBLICATIONS

Gospodarowicz et al. *Endocrine Reviews* 8(2):95–114 (1987).

*Primary Examiner*—David L. Fitzgerald
*Assistant Examiner*—Elizabeth C. Kemmerer
*Attorney, Agent, or Firm*—Hill, Steadman & Simpson

[57] ABSTRACT

A bone growth promoting composition, comprising a content of at least one substance from the group consisting of the growth factors FGF, TGF-β, IGF-II, PDGF and biologically active mutants and fragments thereof and bone extracts with the corresponding activity as well as a bone extract with BMP activity. In combination with an appropriate application material, the use of the composition in the preparation of implant material is also described.

4 Claims, 1 Drawing Sheet

BONE IMPLANT COMPOSITION COMPRISING A POROUS MATRIX, BONE GROWTH PROMOTER PROTEINS, AND PHOSPHOTYROSYL PROTEIN PHOSPHATASE INHIBITOR

This application is a continuation of application Ser. No. 08/387,137, filed Feb. 10, 1995, now abandoned, which is a continuation of application Ser. No. 08/050,405, filed Aug. 20, 1993, now abandoned, which was filed under 35 U.S.C. §371 from PCT/DE92/00780, filed Sep. 9, 1992.

BACKGROUND OF THE INVENTION

The invention relates to a bone growth promoting composition, in particular for use in the preparation of implant material.

Implant material currently in use is composed of autologous bone material, heterologous bone material, or some form of hydroxyapatite. The basis for using such implant material is that this material will promote healing of a osseous defect more rapidly than if the osseous defect is left untreated. Various types of implants will, thus, speed up the filling in of the osseous defect. Because of the inability to obtain sufficient autologous implant material, hydroxyapatite forms of implant material are now being widely used. The problem with hydroxyapatite forms of implant material, however, is that they are not incorporated by osseous ingrowth as rapidly as one would like, thus prolonging the disability of the patient.

International Patent Application WO88/00205 discloses that certain bone morphogenic proteins, namely BMP-1, BMP-2 Class I, BMP-2 Class II, BMP-3, and mixtures thereof in a pharmaceutically acceptable vehicle are useful in the research and treatment of bone and periodontal defects. Furthermore, this application proposes to add a matrix capable of delivering the composition to the site of the bone defect and providing a structure for inducing bone formation, for example hydroxyapatite.

SUMMARY OF THE INVENTION

It is the object of the present invention for to provide for a composition comprising an appropriate application material, such as hydroxyapatite, for bone growth, improved to promote an optimum ingrowth of bone into that material.

According to the present invention, this object is achieved by a content of at least one substance from the group composed of the growth factors FGF, TGF-$\beta$, IGF-II, PDGF and biologically active mutants and fragments thereof as well as bone extracts with the corresponding activity including a bone extract with BMP activity, in combination with an appropriate application material. Surprisingly, it has been shown that it is not only the known proteins of, International Patent Application WO88/00205 which can promote the ingrowth of bone into appropriate application material, but that this object is also achieved by further growth factors, namely FGF, TGF-$\beta$, IGF-II PDGF and biologically active mutants and fragments thereof and by bone extracts with the corresponding activity as well as by bone extracts with BMP activity.

In a preferred embodiment, the application material is hydroxyapatite. Moreover, the application material may be porous, preferably having an adjustable pore size.

For purposes of the present invention, the most preferred application materials consist of algae, coral and/or mussel derivative(s), such as known for example from U.S. Pat. No. 3,929,971 or from German Patent 35 42 744. Such a material has been proved as being extremely useful as a bone implant material.

Preferably, the composition of the invention comprises a content of at least one salt from the group consisting of vanadates, molybdates and fluorides. While it is already known (European Patent Application 0 289 314) that the combination of IGF-II and fluoride is effective in increasing the proliferation of bone cells, it has surprisingly been shown that each of the combinations of at least one of the growth factors (or of the biologically active mutants or fragments or bone extracts) and at least one of the salts are effective in this respect to an at least a comparable level.

In an attempt to explain these findings, we believe that the potentiating effect of fluoride, vanadate, or molybdate compounds is due to their inhibitory action on phosphotyrosyl protein phosphatase. This latter enzyme acts to dephosphorylate phosphoproteins induced by mitogenic signals, thereby inactivating these mitogenic signals. By inhibiting this dephosphorylation, one then promotes the mitogenic signal which is created by the growth factor(s).

In a preferred embodiment of the invention, BMP or a biologically active mutant or fragment thereof is contained in the place of or additionally to one of the growth factors or the biologically active mutants or fragments thereof.

Preferably, the vanadate, molybdate or fluoride ion is associated with a cation, selected from the group consisting of sodium, potassium, calcium, magnesium, and ammonium, which are physiologically particularly acceptable cations.

Furthermore, the invention proposes to use a composition with a content of at least two of the substances from the group consisting of the growth factors FGF, TGF-$\beta$, IGF-II, PDGF, BMP and biologically active mutants and fragments thereof as well as bone extracts with the corresponding activity; preferably four growth factors in combination. In these compositions, it has been shown that the combination of two or more of the growth factors (one or more thereof optionally being replaced by a biologically active mutant or fragment) not only has an additive effect on the proliferation and differentiation of bone cells, but creates a surprisingly marked synergism as well.

In yet another embodiment, the composition of the present invention is used for the preparation of implant material.

DETAILED DESCRIPTION OF THE PRESENTLY PREFERRED EMBODIMENTS

The growth factor for use in the composition of the present invention may be prepared by a number of different methods.

First, in accordance with the present invention, at least one of the growth factors may be isolated from natural, preferably human bone materials, as described for IGF-II by Mojan et al., Biochem. Biophys. Acta 884, 234 (1986).

Alternatively, the growth factors may also be isolated from bone cells grown in culture.

The second way for in which to recover the growth factors is their isolation from serum, including human, bovine, ovine, porcine or equine serum, using conventional techniques.

The third and what may ultimately be the preferred method of preparation involves recombinant DNA techniques, i.e. the recovery of the growth factors or the biologically active mutants of fragments thereof as recombinants from genetic engineering processes. Some of the techniques for example are described for IGF-II in the above mentioned European Patent Application 0 289 314, and for BMP in the above mentioned International Patent Application WO88/00205.

The composition according to the present invention may be characterized by a content of a mitogenic bone extract. The preparation of such an effective bone extract, containing one or more of the growth factors, can be done according to conventional techniques.

The present invention is also directed to the use of the inventive composition for the preparation of an implant material. The composition according to the present invention promotes the optimum ingrowth of bone into the implant material with the ultimate accomplishment of an rapid filling in of for example a osseous defect. One way of preparing such an implant material is to coat one of the inventive combinations of one or more of the growth factors or biological active mutants of fragments thereof or of a corresponding bone extract, optionally combined with one of the salts from the group of vanadates, molybdates, and fluorides, to porous hydroxyapatite granules as an application material. It has been shown that a surgically created osseous defect is healing more rapidly and more completely with such hydroxyapatite granules as compared with hydroxyapatite alone.

The invention is now further illustrated by the following examples.

EXAMPLE 1

FGF increases proliferation of normal human bone cells.

Figure 1:
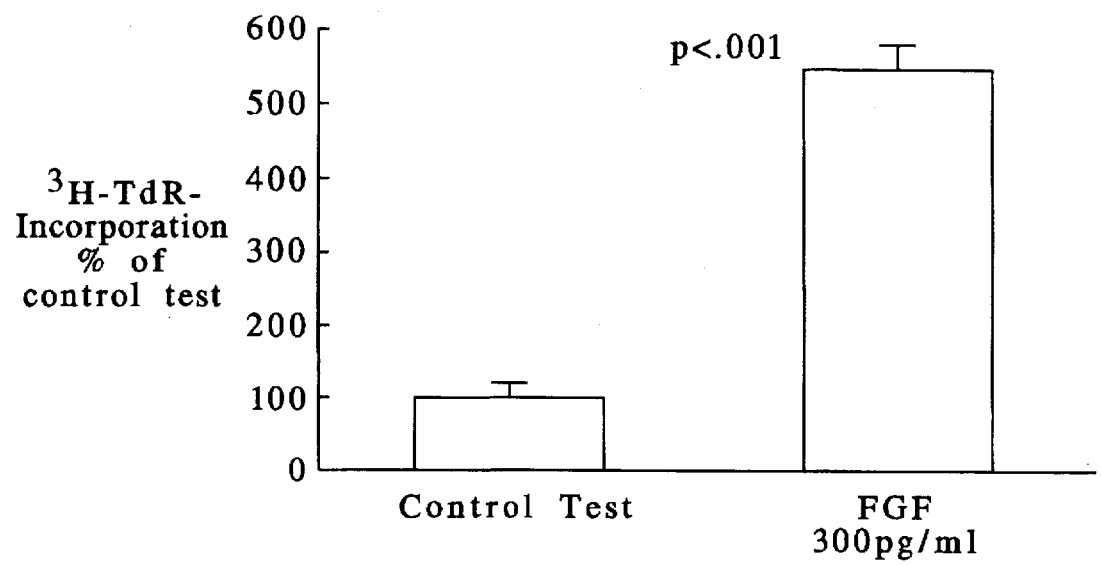
FIG. 1 is a graph illustrating cell proliferation as a function of the incorporation of tritiated thymidine into DNA. Human bone cells were treated with 300 pg/ml of the growth factor, FGF. Control cultures were also run.

Cell proliferation was assessed by incorporation of tritiated thymidine into DNA. Cells were exposed to FGF for 16 hours and then labeled with 0.75 microcuries of tritiated thymidine. After two hours, the medium was drawn off and the cells rinsed twice with phosphate buffered saline. The amount of TCA insoluble radioactivity was then measured as an index for DNA synthesis. The amount of FGF added was 300 pg/ml. For these studies, the human bone cells were cultured in serum free DMEM medium. As shown in FIG. 1, there was a five fold increase in cell profileration in cultures treated with FGF compared to the control.

EXAMPLE 2

PDGF increases proliferation of normal human bone cells.

Figure 2:
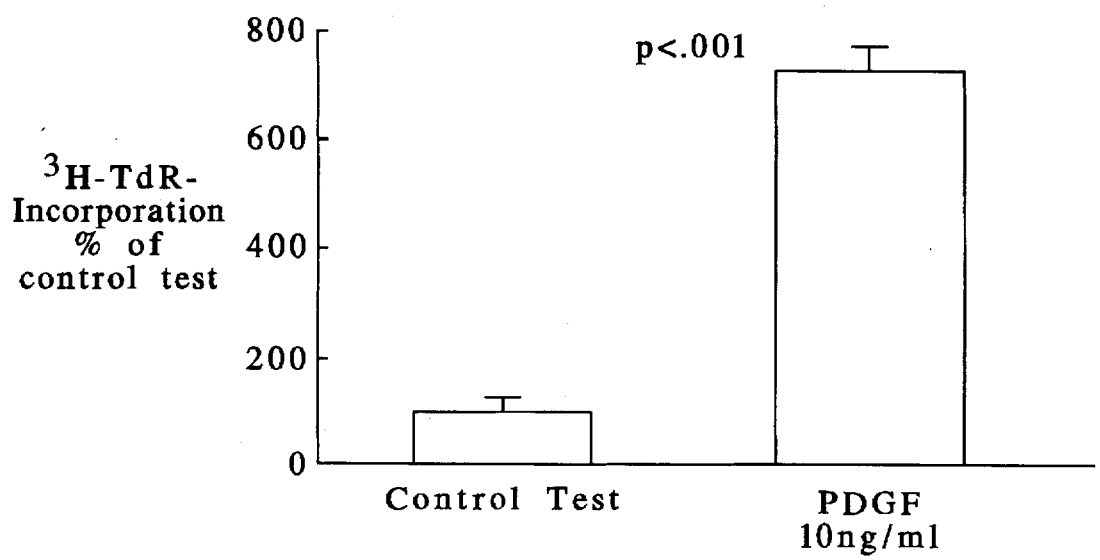
FIG. 2 is a graph illustrating cell proliferation as a function of the incorporation of tritiated thymidine into DNA. Human bone cells were treated with 10 ng/ml of the growth factor, PDGF. Control cultures were also run.

Cell proliferation was assessed by incorporation of tritiated thymidine into DNA. Cell were exposed to PDGF for 16 hours and then labeled with 0.75 microcuries of tritiated thymidine. After two hours, the medium was drawn off and the cells rinsed twice with phosphate buffered saline solution. The amount of TCA insoluble radioactivity was then measured as an index for DNA synthesis. The amount of PDGF added was 10 ng/ml. For these studies, the human bone cells were cultured in serum free DMEM medium. As shown in FIG. 2, there was a seven fold increase in cell proliferation in cultures treated with PDGF compared to the control.

EXAMPLE 3

Comparable results were obtained with TGF-β, IGF-II and bone extract with corresponding activity or BMP activity and mixtures thereof.

EXAMPLE 4

For application of the present invention, 750 µg hydroxyapatite was complexed with 250 µg of sodium fluoride and 200 ng of FGF, TGF-β, IFG-II, PDGF, bone extract with corresponding activity or BMP activity, or mixtures thereof to prepare an implant. Such implants have proven useful for the treatment of bone defects such as nonunion fractures, any defects in bone with trauma or surgery, in association from cancer, any defects from infection (osteomyelitis), alveolar defects due to periodontal disease and congenital anomalies. With all of the implants tested, bone ingrowth was significantly enhanced.

The inventive features disclosed in the preceding description, as well as in the claims and drawings can be essential to the realization of the invention in its various embodiments, either singly or in the form of random combinations.

We claim:

1. A method for making a bone implant material comprising: providing a porous matrix material; and thereafter coating the matrix material with at least one bone growth promoter selected from the group consisting of FGF TGF-β, IGF-II, PDGF and BMP, and a phosphotyrosyl protein phosphatase inhibitor selected from the group consisting of vanadate and molybdate salts, with the proviso that when the bone growth promoter is IGF-II, the phosphotyrosyl protein phosphatase inhibitor is not ortho-vanadate.

2. A method for treating an osseous defect comprising: applying a bone implant composition directly to the site of the osseous defect, said bone implant composition comprising: (a) a porous matrix material; (b) at least one bone growth promoter protein selected from the group consisting of FGF, TGF-β, IGF-II, PDGF and BMP; and (c) a phosphotyrosyl protein phosphatase inhibitor selected from the group consisting of vanadate and molybdate salts, with the proviso that when the bone growth promoter is IGF-II, the phosphotyrosyl protein phosphatase inhibitor is not ortho-vanadate.

3. A bone implant composition for application to the site of an osseous defect, said implant composition comprising:

a porous matrix material selected from the group consisting of hydroxyapatite, algae, coral derivatives and mussel derivatives;

a bone growth promoting amount of at least one bone growth promoter protein selected from the group consisting of FGF, TGF-β, IGF-II, PDGF and BMP; and an amount of a phosphotyrosyl protein phosphatase inhibitor selected from the group consisting of vanadate and molybdate salts, with the proviso that when the bone growth promoter protein is IFG-II, the phosphotyrosyl protein phosphatase inhibitor is not ortho-vanadate, such that the combination of the bone growth promoter protein and the phosphotyrosyl protein phosphatase inhibitor together provide an improvement in bone growth proliferation as measured by $^3$H-thymidine uptake and alkaline phosphatase activity, as compared to a composition containing the porous matrix material and the bone growth promoter protein or the porous matrix material and the phosphotyrosyl protein phosphatase inhibitor alone.

4. A bone implant composition as defined in claim 3, wherein the porous matrix material has an adjustable pore size.

* * * * *